US012576242B2

(12) United States Patent
Sharma

(10) Patent No.: US 12,576,242 B2
(45) Date of Patent: Mar. 17, 2026

(54) MEDICAL SYSTEMS, DEVICES, AND RELATED METHODS

(71) Applicant: Boston Scientific Medical Device Limited, Galway (IE)

(72) Inventor: Deepak Kumar Sharma, Muzaffarnafar (IN)

(73) Assignee: Boston Scientific Medical Device Limited, Galway (IE)

( * ) Notice: Subject to any disclaimer, the term of this patent is extended or adjusted under 35 U.S.C. 154(b) by 931 days.

(21) Appl. No.: 17/855,348

(22) Filed: Jun. 30, 2022

(65) Prior Publication Data

US 2023/0001148 A1     Jan. 5, 2023

Related U.S. Application Data

(60) Provisional application No. 63/217,325, filed on Jul. 1, 2021.

(51) Int. Cl.
*A61M 25/01* (2006.01)

(52) U.S. Cl.
CPC . *A61M 25/0136* (2013.01); *A61M 2025/0166* (2013.01)

(58) Field of Classification Search
CPC .......... A61M 25/0127; A61M 25/0158; A61B 2017/00411; A61B 34/73; A61B 34/20
See application file for complete search history.

(56) References Cited

U.S. PATENT DOCUMENTS

| | | | |
|---|---|---|---|
| 7,778,688 B2 * | 8/2010 | Strommer ............ | A61B 6/5247 |
| | | | 600/424 |
| 10,820,947 B2 * | 11/2020 | Julian ................ | A61G 13/1295 |
| 2007/0250041 A1 * | 10/2007 | Werp ................ | A61M 25/0127 |
| | | | 604/529 |
| 2009/0043246 A1 * | 2/2009 | Dominguez ........... | A61B 34/70 |
| | | | 604/21 |
| 2012/0130218 A1 * | 5/2012 | Kauphusman ....... | A61B 5/6852 |
| | | | 600/585 |
| 2017/0007254 A1 | 1/2017 | Jaworek et al. | |
| 2018/0161110 A1 | 6/2018 | Overmyer et al. | |

FOREIGN PATENT DOCUMENTS

| | | |
|---|---|---|
| EP | 2 393 428 | 12/2011 |

OTHER PUBLICATIONS

International Search Report and Written Opinion issued in International Application No. PCT/IB2022/056157, issued Oct. 4, 2022 (11 pages).

* cited by examiner

*Primary Examiner* — Laura A Bouchelle
(74) *Attorney, Agent, or Firm* — Bookoff McAndrews PLLC

(57) ABSTRACT

A medical device for insertion into a body may include a handle assembly including a handle body and a ball joint; a sensor assembly configured to electronically communicate with a magnet; a body extending longitudinally from the handle assembly; an articulation portion coupled to a distal end of the body, wherein the articulation portion includes a magnetic material; and an end effector coupled to a distal end of the articulation portion. The articulation portion may be configured to move upon application of a magnetic field from the magnet.

18 Claims, 4 Drawing Sheets

MEDICAL SYSTEMS, DEVICES, AND RELATED METHODS

CROSS REFERENCE TO RELATED APPLICATION

This application claims priority to U.S. Provisional Application No. 63/217,325, filed Jul. 1, 2021, the entirety of which is incorporated by reference herein.

TECHNICAL FIELD

This disclosure generally relates to medical systems, devices, and related methods that may be used to treat a subject. Aspects of the disclosure relate to medical systems, devices, and methods for endoscopic medical procedures, such as manipulating and cutting tissue with one or more medical devices during resection and dissection procedures, among other aspects.

BACKGROUND

A wide variety of medical techniques and instruments have been developed for diagnosis and/or treatment within a patient's body, such as within a patient's gastrointestinal (GI) tract. Endoscopic sub-mucosal dissection (ESD), endo-scopic sub-mucosal resection (ESR), mucosal resection (EMR), polypectomy, mucosectomy, etc., are minimally invasive treatment methods for both malignant and non-malignant lesions. Endoscopic medical procedures, such as, for example, ESR, may be used to excise sessile adenomas or other unwanted tissue (e.g., tumors attached to a bodily surface) from the surface of an anatomical lumen (e.g., stomach, esophagus, colon, etc.). Such procedures often require multiple endoscopic instruments for the resection of tissue. In some instances, a grasper is used with either a cautery knife or snare during such medical procedures, for resecting tissue from a treatment site. However, many con-ventional graspers operate in only one degree of freedom, and deflection of the grasper (or another end effector) is often limited and/or dependent on the tip deflection of an endoscope or other device used for insertion into the patient.

Additionally, deflecting and/or repositioning the grasper or other end effector relative to the treatment site may require the user to deflect and/or reposition the endoscope relative to the treatment site, which may affect the visual-ization of the treatment site. These concerns may increase the duration, costs, and risks of the medical procedure. The systems, devices, and methods of this disclosure may rectify some of the deficiencies described above or address other aspects of the art.

SUMMARY

Examples of the disclosure relate to, among other things, systems, devices, and methods for performing one or more medical procedures with the medical systems and devices. Each of the examples disclosed herein may include one or more of the features described in connection with any of the other disclosed examples.

In some aspects, a medical device for insertion into a body may include a handle assembly including a handle body and a ball joint; a sensor assembly configured to electronically communicate with a magnet; a body extending longitudi-nally from the handle assembly; an articulation portion coupled to a distal end of the body, wherein the articulation portion includes a magnetic material; and an end effector coupled to a distal end of the articulation portion. The articulation portion may be configured to move upon appli-cation of a magnetic field from the magnet.

In other aspects, the medical device may include one or more of the following features. The ball joint may be positioned within the sensor assembly. The sensor assembly may comprise a cylindrical body including a central lumen, wherein a portion of the handle assembly is positioned within the central lumen; and a plurality of sensor actuators positioned facing the handle assembly. The handle assembly may include a cylindrical portion configured to actuate one or more of the plurality of sensors when the handle body is pivoted towards the sensor assembly. The plurality of sensor actuators may be evenly spaced circumferentially around a central longitudinal axis of the handle assembly. The handle assembly may include a first actuator and a second actuator, and wherein each of the first actuator and the second actuator engage a single actuation wire. The sensor assembly may include a controller configured to wirelessly communicate with a controller associated with the magnet. The body may comprise a coil, a braid layer extending around the coil, an exterior layer extending around the braid layer, and a central lumen configured to receive an actuation wire. The articu-lation portion may include a rectangular strip of magnetic material wound in a helical shape. The end effector may include stainless steel or Nitinol.

In other aspects, the medical device may include one or more of the following features. The handle body may include a ball portion at a distal end of the handle body; a cylindrical portion coupled to the ball portion; a first slot configured to receive a first actuator; a second slot config-ured to receive a second actuator; and a ring portion at a proximal end of the handle body. The sensor assembly may comprise a cylindrical body including a central lumen, wherein a portion of the handle assembly is positioned within the central lumen; and a plurality of sensor actuators positioned on the cylindrical body and facing the handle assembly, wherein the plurality of sensor actuators are positioned around the cylindrical portion and proximal from the ball joint. The medical device may further include an articulation wire extending from the end effector, through the body and the sensor assembly, and coupled to a portion of the handle assembly. The handle assembly may be configured to pivot relative to the sensor assembly. The end effector may be rotatable, about a central longitudinal axis of the medical device, relative to the articulation portion.

In other aspects, a medical system may include a medical device comprising: a handle assembly; a sensor assembly configured to communicate with a magnet assembly and coupled to the handle assembly; a body extending longitu-dinally from the handle assembly; and an articulation por-tion coupled to a distal end of the body, wherein the articulation portion is made of a magnetic material. The magnet assembly may be moveably coupled to a patient table and comprising a plurality of magnets; and the articu-lation portion may be configured to move when the magnet assembly applies a magnetic field to the articulation portion. In some examples, the plurality of magnets are positioned circumferentially around the patient table. The sensor assembly may include a plurality of sensor actuators, and each sensor actuator may be in electronic communication with at least one magnet of the plurality of magnets.

In other aspects, a method of moving a medical device may include: pivoting a handle assembly about a ball joint; engaging at least one sensor actuator of a sensor assembly with the handle assembly; activating a electromagnet via the engaged at least one sensor actuator; and moving an articulation section via a magnetic field induced by activating the electromagnet, wherein the articulation section is a magnetic material. In some examples, the method may further include positioning a magnet assembly proximate to a target area, wherein the articulation section is positioned at the target area and the magnet assembly includes the electromagnet.

It may be understood that both the foregoing general description and the following detailed description are exemplary and explanatory only and are not restrictive of this disclosure, as claimed.

BRIEF DESCRIPTION OF THE DRAWINGS

The accompanying drawings, which are incorporated in and constitute a part of this specification, illustrate exemplary aspects of the disclosure and together with the description, serve to explain the principles of the disclosure.

DETAILED DESCRIPTION

The terms "proximal" and "distal" are used herein to refer to the relative positions of the components of an exemplary medical system and exemplary medical devices. When used herein, "proximal" refers to a position relatively closer to the exterior of the body of a subject or closer to a medical professional using the medical system or medical device. In contrast, "distal" refers to a position relatively further away from the medical professional using the medical system or medical device, or closer to the interior of the body of the subject. Proximal and distal directions are labeled with arrows marked "P" and "D", respectively, throughout the figures. As used herein, the terms "comprises," "comprising," "having," "including," or other variations thereof, are intended to cover a non-exclusive inclusion, such that a system, device, or method that comprises a list of elements does not include only those elements, but may include other elements not expressly listed or inherent thereto. Unless stated otherwise, the term "exemplary" is used in the sense of "example" rather than "ideal." As used herein, the terms "about," "substantially," and "approximately," indicate a range of values within +/−10% of a stated value.

Embodiments of this disclosure include devices, systems, and methods for manipulating, cutting, grabbing, ligating, and/or otherwise treating tissue. In some examples, the devices, systems and/or methods discussed herein may be utilized during endoscopic mucosal resection (EMR) and/or endoscopic submucosal dissection (ESD) procedures. In examples, EMR and ESD include endoluminal placement of one or more devices for grasping and cutting tissue proximate to a target area within the body of a patient. Placement of the one or more medical devices may be via a catheter, scope (endoscope, bronchoscope, colonoscope, gastroscope, duodenoscope, etc.), tube, or sheath, inserted into the GI tract via a natural orifice or incision. The orifice can be, for example, the nose, mouth, or anus, and the placement can be in any portion of the GI tract, including the esophagus, stomach, duodenum, large intestine, or small intestine. Placement also can be in other organs reachable via the GI tract. The patient's tissue may be grasped using suction from one or more medical devices and/or a grasper, and then the tissue may be cut by a cutting device for subsequent removal from the patient's body. Although EMR and ESD are discussed herein, the disclosure is not so limited. Embodiments of the disclosure include devices and systems that may be used in any suitable procedure in any body lumen or organ.

Reference will now be made in detail to examples of this disclosure described above and illustrated in the accompanying drawings. Wherever possible, the same reference numbers will be used throughout the drawings to refer to the same or like parts.

Figures 1, 2A, 2B:
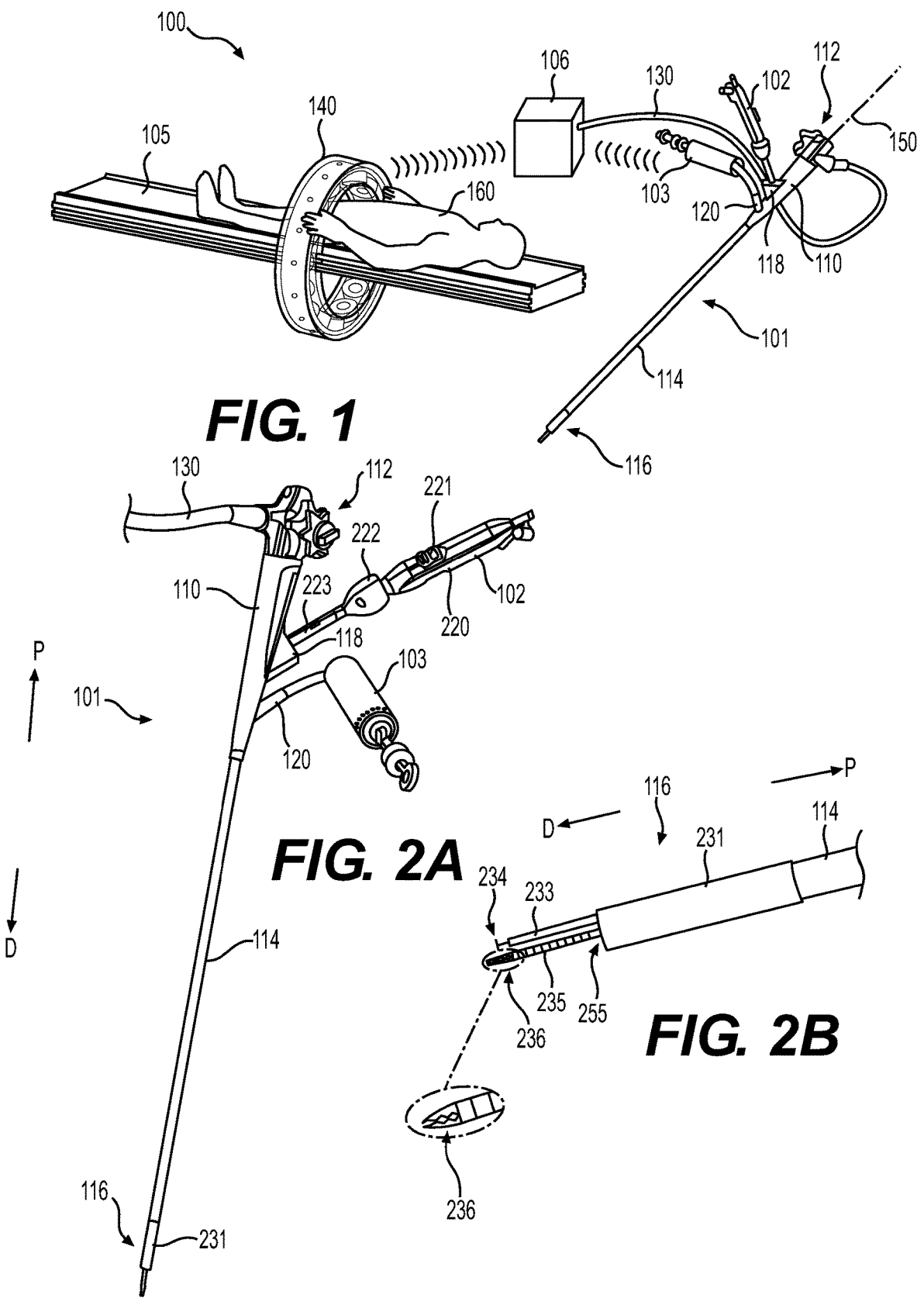
FIG. 1 illustrates a perspective view of a medical system, according to aspects of this disclosure.
FIG. 2A illustrates a perspective view of three exemplary medical devices of the medical system of FIG. 1, according to aspects of this disclosure.
FIG. 2B illustrates distal portions of the medical devices shown in FIG. 2A, according to aspects of the disclosure.

FIG. 1 illustrates a perspective view of an exemplary medical system 100 including an endoscope 101, a first medical device 102, a second medical device 103, a patient table 105, and a control unit 106. Although medical device system 100 is shown with endoscope 101, any other similar insertion device may be used in medical system 100, such as a bronchoscope, colonoscope, gastroscope, duodenoscope, etc. Endoscope 101 may include a handle 110, one or more actuators 112, and a body 114 extending from handle 110 to a distal end 116. A first working channel may extend from a first working channel port 118 to an opening at distal end 116, and a second working channel may extend from a second working channel port 120 to an opening at distal end 116. Distal end 116 of endoscope 101 may also include a camera, and movement of distal end 116 and functionality of the camera may be controlled via one or more actuators 112 on handle 110 and/or one or more actuators of control unit 106. Actuators 112 may include knob actuators, button actuators, and any other types of actuators known in the art.

An umbilicus 130 may connect endoscope 101 to one or more of control unit 106, a fluid source, a suction source, and/or other exterior devices such as a monitor for viewing images from a camera. Control unit 106 may be connected to umbilicus 130 or may be wirelessly connected to endoscope 101, and may control any aspect of endoscope 101, such as the camera. Endoscope 101 may have a central longitudinal axis 150 extending longitudinally through a central portion of handle 110 and body 114. As shown in FIG. 1, in some embodiments, a patient 160 may be positioned on patient table 105 and magnet assembly 140 may be positioned around the patient 160 during a medical procedure. In some examples, control unit 106 may communicate wirelessly with magnet assembly 140 and control movement of magnet assembly 140 relative to patient table 105. For example, control unit 106 may send instructions to a controller 390 of magnet assembly 140 to activate one or more motors to move magnet assembly 140 along rail portions 310, 320 of patient table 105. Medical system 100 may be used to conduct medical procedures, such as endoscopic tissue resection procedures or any other medical procedure. Further discussion of the devices and methods of medical system 100 are discussed herein below.

FIG. 2A illustrates endoscope 101 with first medical device 102 and second medical device 103 positioned within working channels of endoscope 101, and distal portions of first medical device 102 and second medical device 103 extending out of distal openings of each working channel in endoscope 101. First medical device 102 may include a handle 220, a coupler 223, and a body 233 (FIG. 2B) configured to extend through a working channel of endoscope 101. Handle 220 may include an actuator 221, and in some examples actuator 221 may control the supply of electrical energy to a distal end effector 234 (FIG. 2B) of first medical device 102. Coupler 223 may couple first medical device 102 to handle 110 of endoscope 101. A pivot joint 222 may couple handle 220 to coupler 223, and handle 220 may pivot about pivot joint 222 to initiate movement of end effector 234 and/or a distal portion of body 233. First medical device 102 may include articulation wires positioned within body 233 and coupled to handle 220, and articulation wires may control the movement of end effector 234 and/or the distal portion of body 233 via pivoting handle 220. For example, the articulation wires may bend a distal portion of body 233 when a user pivots handle 220 about pivot joint 222. In some examples, actuation of actuator 221 may supply electrical energy to end effector 234 for cutting or cautery of a patient's tissue.

FIG. 2B shows distal end 116 of endoscope 101 shown in FIG. 2A. As shown in FIG. 2B, a distal portion of body 233 of first medical device 102 may extend distally from distal end 116 of endoscope 101, and end effector 234 may be a T-shaped electrode configured to cut tissue via electrical energy. It is understood that other shapes of electrodes, and other types of end effectors, are within the scope of this disclosure. A distal portion of body 235 of second medical device 103 may extend distally from a distal end of body 114, and an end effector 236 of second medical device 103 may be a grasper configured to grasp and release tissue. A magnetic shield 231 may be positioned around a distal portion of body 114 (e.g., distal end 116). Magnetic shield 231 may be cylindrical or tubular with a central lumen extending longitudinally through magnetic shield 231. Magnetic shield 231 may be configured to fit around the distal end 116 of body 114 such that a distal face 255 of body 114 is exposed (e.g. not covered by magnetic shield 231) and a radially-outer surface, relative to axis 150, of body 114 is covered by magnetic shield 231. In other words, distal face 255 of body 114 may substantially align with or be coplanar with a distal end face of magnetic shield 231. Magnetic shield 231 may be copper or any other material configured to prevent a magnetic field from penetrating through the material. Placement of magnetic shield 231 over a distal portion of body 114 may protect components, such as a camera or light sources, at a distal end of endoscope 101 from a magnetic field. In some examples, the portion of body 114 covered by magnetic shield 231 may be plastic.

Figures 3, 4, 5, 6, 7, 8:
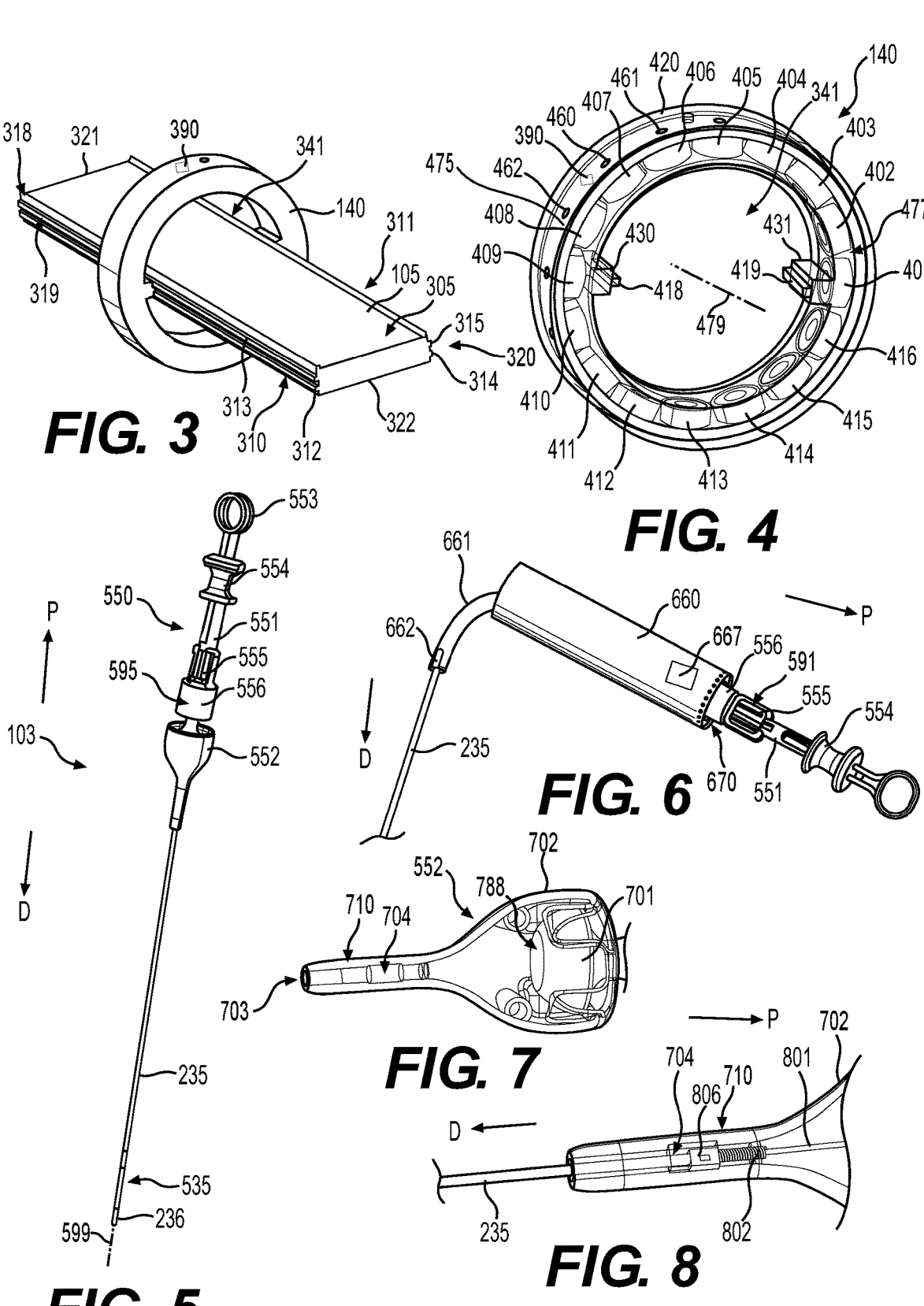
FIG. 3 illustrates a perspective view of a patient table of the medical system of FIG. 1, according to aspects of the disclosure.
FIG. 4 illustrates a perspective view of an exemplary magnetic assembly of the medical system of FIG. 1, according to aspects of this disclosure.
FIG. 5 illustrates a medical device with a component removed to expose internal portions of the medical device, according to aspects of this disclosure.
FIG. 6 illustrates a proximal end portion of an exemplary medical device, according to aspects of this disclosure.
FIG. 7 illustrates a ball joint of the medical device of FIG. 6, according to aspects of this disclosure.
FIG. 8 illustrates a portion of the medical device of FIG. 6, according to aspects of this disclosure.

FIG. 3 shows a perspective view of patient table 105 and magnetic assembly 140. Patient table 105 may be sized to allow a patient to lie down on a top surface 305 of patient table 105, and in some examples, patient table 105 may include legs (not shown). Patient table 105 may be a non-magnetic material such as aluminum, wood, steel, etc. Patient table 105 may include a first rail portion 310 and a second rail portion 311. The first rail portion 310 may be positioned at an opposing side of patient table 105 from the second rail portion 311. Each of first rail portion 310 and second rail portion 311 may include two protrusions 312, 313, 314, 315 extending outward from a side surface 318 of patient table 105. A space 319 between protrusions 312, 313 may be configured to receive a first protrusion 418 (FIG. 4) of magnet assembly 140, and a space 320 between protrusions 314, 315 may be configured to receive a second protrusion 419 (shown in FIG. 4) of magnet assembly 140. First rail portion 310 and second rail portion 311 may extend longitudinally from a first end 321 to a second end 322 of patient table 105, and the first end 321 may be at an opposite end from the second end 322. Magnet assembly 140 may be moveably coupled to patient table 105, and may extend around patient table 105. For example, magnet assembly 140 may at least partially or fully encircle patient table 105. A central lumen 341 may extend through magnet assembly 140, and patient table 105 may be positioned within central lumen 341. Magnet assembly 140 may be configured to move along first rail portion 310 and second rail portion 311 to adjust a longitudinal position of magnet assembly 140 along a length of patient table 105 between first end 321 and second end 322. A controller 390 may be electronically connected to each of the magnets 401-416 of magnet assembly 140 and may control each of the magnets 401-416 of magnet assembly and any other electrical components of magnet assembly 140.

FIG. 4 shows magnet assembly 140 with portions of magnet assembly 140 transparent to show internal magnets 401-416 positioned within body 420. Body 420 may be circular and may include a circular internal cavity 477 in which magnets 401-416 are positioned. Body 420 may include vent openings 460, 461, 462 spaced circumferentially about a radially-outer surface 475 of body 420. While vent openings 460-462 are depicted as symmetrically spaced, in other embodiments, asymmetrical spacing is contemplated, such as if magnets are only positioned at specific areas within magnet assembly 140. Vent openings 460, 461, 462 may facilitate cooling magnets 401-416 and may increase airflow into and out of internal cavity 477. Each of magnets 401-416 may be electromagnets and may be controllable via control unit 106 (FIG. 1). Each magnet 401-416 may be independently controllable via control unit 106 and/or controller 390. In some examples, one or more sensor actuators of second medical device 103 may control one or more magnets 401-416, either directly or through control unit 106 and/or controller 390. Magnets 401-416 may form a circular ring-shape around patient table 105, each magnet 401-416 may be one or more electromagnets.

Rail portions 430, 431 may extend radially-inward towards a central axis 479 and may be positioned at a radially-inward facing surface of magnet assembly 140. Each rail portion 430, 431 may include a protrusion 418, 419 extending radially-inward towards central axis 479 of lumen 341. Protrusions 418, 419 may be configured to be received by, and move within, first rail portion 310 and second rail portion 311, respectively. For example, protrusion 418 may slide between protrusions 312, 313, and protrusion 419 may slide between protrusions 314, 315 when magnet assembly 140 is moved in a longitudinal direction over patient table 105. As noted above, magnet assembly 140 may include controller 390, which may be, wirelessly or via one or more wires, connected to each magnet 401-416, and controller 390 may wirelessly, or via one or more wires, communicate with control unit 106. In other examples, controller 390 may be positioned external from body 420, such as positioned within patient table 105.

Turning to FIG. 5, second medical device 103 may include a handle assembly 550, a body 235, a sensor assembly 660, coupler 661, and an end effector 236. FIG. 5 shows a perspective view of second medical device 103 with sensor assembly 660 and coupler 661 removed. Body 235 may be cylindrical and may extend longitudinally to end effector 236 at a distal end of body 235. Body 235 may include an articulation section 535, which will be discussed in further detail below with reference to FIG. 14. Second medical device 103 does not include articulation wires for moving articulation section 535.

Handle assembly 550 may include a body 551 including a ring portion 553, a first actuator 554, a second actuator 555, a cylindrical portion 556, and a ball joint 552. Ring portion 553 may be at a proximal end of body 551 and may be configured to receive one or more of a user's fingers or thumb. First actuator 554 may extend circumferentially around body 551. First actuator 554 may translate in a proximal or distal direction along body 551 to actuate end effector 236. For example, moving first actuator 554 distally along body 551 may open a grasper (end effector 236), and moving first actuator 554 proximally along body 551 may close the grasper (end effector 236). In some examples, first actuator 554 may include a lock button (not shown) to lock the position of first actuator relative to body 551. A lock button on first actuator 554 may extend perpendicular to axis 599 and may include first state in which a pin extends to engage body 551 to prevent movement of first actuator 554 in the proximal or distal directions, and a second state in which the pin may be released from engagement with body 551.

Second actuator 555 may rotate about central longitudinal axis 599 of second medical device 103. Second actuator 555 may be configured to rotate end effector 236 about central longitudinal axis 599. In some examples, second actuator 555 may include ridges 591 extending longitudinally along a radially-outer surface of second actuator 555 relative to central longitudinal axis 599, and ridges 591 (FIG. 6) may be configured to facilitate traction and/or grip of a user's fingers or thumb on second actuator 555. Second actuator 555 may be positioned distal to first actuator 554, and portions of body 551 may extend around second actuator 555 such that second actuator 555 is positioned within a slot 592 (shown in FIG. 9) of body 551. Second actuator 555 may comprise two half components that are snap-fit together.

Cylindrical portion 556 of handle assembly 550 may be distal to the second actuator 555 and proximal from ball joint 552. Cylindrical portion 556 may be integral with and/or fixedly coupled to body 551, and may be configured to engage with sensor assembly 660. As shown in FIG. 6, cylindrical portion 556 may be positioned within a central lumen 670 of sensor assembly 660, at a proximal end of sensor assembly 660. A radially-outward facing surface 595 (FIG. 5), relative to central axis 599, of cylindrical portion 556 may be substantially parallel to central axis 599. Cylindrical portion 556 may be configured to engage sensor assembly 660, and this engagement will be discussed in further detail with relation to FIGS. 10A-11.

As shown in FIG. 6, coupler 661 may be flexible and may couple to a working channel port 118, 120 of endoscope 101. For example, a coupling feature 662 may snap-fit onto a working channel port 118, 120 to secure coupler 661 to endoscope 101. In some examples, coupling feature 662 may include a plurality of slots in the distal end of coupler 661. Coupling feature 662 may bend outward from coupler 661 to fit over a portion of a working channel port 118, 120 and snap-fit onto the working channel port 118, 120. Coupler 661 may include an inner braiding lining, and may extend around body 235. In some examples, coupler 661 may be PEBAX® or another thermoplastic elastomer.

Figures 9, 10A, 10B, 11, 12:
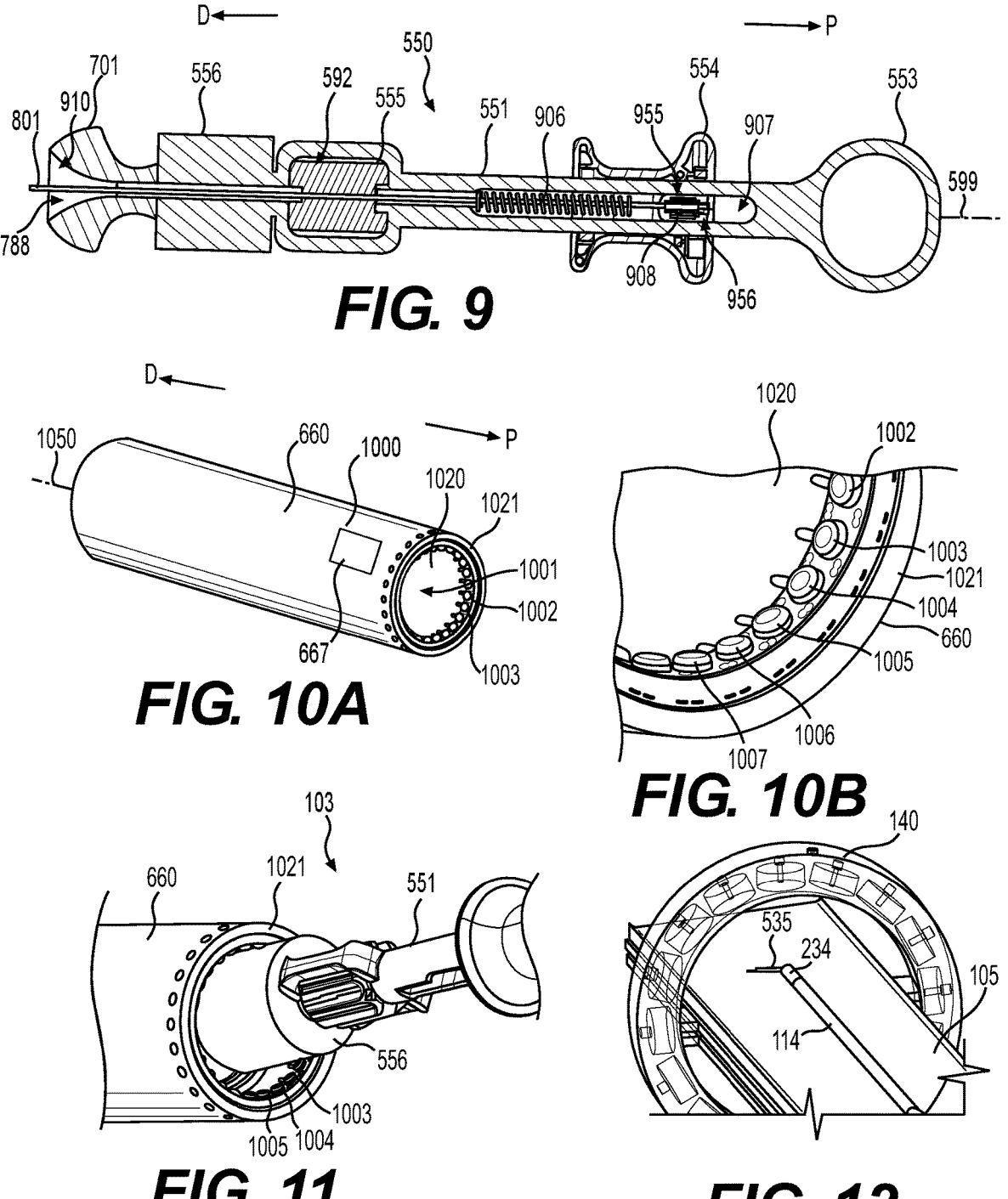
FIG. 9 illustrates a side, partial cross-sectional view of a handle assembly of a medical device, according to aspects of this disclosure.
FIGS. 10A and 10B illustrate perspective views of portions of a component of a medical device, according to aspects of this disclosure.
FIG. 11 is a perspective view of a portion of a medical device, according to aspects of this disclosure.
FIG. 12 is a perspective view of a portion of the medical system of FIG. 1, according to aspects of this disclosure.

Ball joint 552 may couple handle assembly 550 to body 235. As shown in FIG. 7, ball joint 552 may include a ball portion 701 and a receiving body 702. Ball portion 701 may be a distal end portion of handle assembly 550, and ball portion 701 may be configured to rotate within receiving body 702 to pivot handle assembly 550 about ball joint 552. Ball portion 701 may be approximately hemispherical-shaped and may engage with a spherical surface of receiving body 702. Ball portion 701 may include a central lumen 788 extending through ball portion 701. A proximal end of ball portion 701 may be coupled to cylindrical portion 556. Central lumen 788 may taper radially-inward toward central axis 599 as central lumen 788 extends proximally through ball portion 701, which is shown in FIG. 9. Receiving body 702 may be configured to receive ball portion 701, and a central lumen 703 may extend through receiving body 702. Central lumen 703 may extend through a neck portion 710 of receiving body 702, and central lumen 703 may be tapered at a distal portion of lumen 703 such that the diameter of lumen 703 through neck portion 710 may be smaller than a proximal portion of lumen 703 outside of neck portion 710. In some examples, receiving body 702 may consist of two portions (halves) that are fitted together via one or more screws.

Ball joint 552 may be positioned within lumen 670 of sensor assembly 660, and receiving body 702 may be fixedly coupled to sensor assembly 660. Receiving body 702 may be pressure fit within sensor assembly 660 such that radially-inward facing surface 1020 contacts receiving body 702 and holds receiving body 702 in place. In some examples, receiving body 702 may be glued or otherwise coupled to sensor assembly 660. For example, as shown in FIG. 6, ball joint 552 may be positioned entirely within lumen 670 of sensor assembly 660. In some examples, ball portion 701 may be friction fit or interference fit with receiving body 702. This coupling of ball portion 701 to receiving body 702 may allow handle assembly 550 to pivot about ball joint 552 relative to sensor assembly 660.

Neck portion 710 may facilitate coupling receiving body 702 to body 235. A cavity 704 of neck portion 710 may be configured to receive a crimp sleeve 806. FIG. 8 illustrates a side view of neck portion 710 with body 235 coupled to receiving body 702 via crimp sleeve 806. Crimp sleeve 806 may be a rectangular crimp sleeve, and crimp sleeve 806 may be sized larger than the distal section of central lumen 703 distal from cavity 704, thus preventing crimp sleeve 806 from moving distally through central lumen 703 beyond cavity 704. An actuation wire 801 may extend through receiving body 702, crimp sleeve 806, and into a central lumen of body 235 to end effector 236. A coil 802 may be positioned around actuation wire 801, and may extend from receiving body 702 to a distal portion of body 235. Actuation wire 801 may be movable distally or proximally through body 235, coil 802, and crimp sleeve 806. In some examples, actuation wire 801 may be Nitinol or Stainless Steel.

FIG. 9 illustrates a side view of handle assembly 550 with body 551, first actuator 554, and second actuator 555 shown in cross-section. Actuation wire 801 may extend through central lumen 788 of body 551 to slot portion 907. A distal end portion 955 of actuation wire 801 may be coupled to a crimp sleeve 908, and the crimp sleeve 908 may be positioned within a cavity 956 of first actuator 554. Crimp sleeve 908 may be sized larger than the diameter of central lumen 788 distal from slot portion 907, and thus may be configured to move within slot portion 907 and engage slot portion 907 at the distal and proximal ends of slot portion 907. Slot portion 907 may be configured to limit the movement of distal portion 955 of actuation wire 801 in both the distal and proximal directions. A biasing member 906, such as a spring, may be positioned distal from crimp sleeve 908 and may bias actuation wire 801 to a proximal position, which in some examples may bias a grasper at distal end of actuation wire 801 towards a closed or an open position. Proximal and distal movement of first actuator 554 may move actuation wire 801 proximally and distally, respectively, which may cause actuation of end effector 236 (e.g., opening or closing of a grasper, etc.).

Second actuator 555 may be coupled to actuation wire 801 and may be configured to rotate actuation wire 801 about central axis 599 to cause rotation of end effector 236 about central axis 599. Second actuator 555 may be directly coupled to actuation wire 801 or may be indirectly coupled to actuation wire 801 through a hypo tube. For example, a hypo tube may be crimped over actuation wire 801, and second actuator 555 be coupled to the square hypo tube. In some examples, the hypo tube may have a polygonal cross-sectional shape to allow edges to engage with second actuator 555 while still allowing translation through the hypo tube. In some examples, second actuator 555 may include two portions, and the two portions may be coupled together to form second actuator 555. Actuation wire 801 may translate proximally or distally through second actuator 555.

Central lumen 788 may extend through cylindrical portion 556 and ball portion 701. An expanded end portion 910 of central lumen 788 may facilitate the prevention of kinking in the articulation wire 801 as handle assembly 550 is pivoted about ball joint 552.

FIG. 10A illustrates a perspective view of sensor assembly 660. Senor assembly 660 may have a cylindrical body 1000 and a central lumen 1001 extending through cylindrical body 1000. A plurality of sensor actuators 1002, 1003 may be positioned circumferentially around a radially-inward facing, relative to central longitudinal axis 1050, surface 1020. Sensor actuators 1002, 1003 may be proximate to a proximal end 1021 of cylindrical body 1000. In some examples, sensor actuators 1002, 1003 may be arranged in a circle extending around central longitudinal axis 1050 and each sensor actuator 1002-1007 may be evenly spaced between two adjacent sensor actuators 1002, 1003. Lumen 1001 may be sized to receive ball joint 552 such that receiving body 702 may couple to sensor assembly 660 via engagement with radially-inward facing surface 1020. FIG. 10B illustrates a magnified view of a proximal portion of sensor assembly 660 with sensor actuators 1002-1007 extending outward from radially-inward facing surface 1020. Each of sensor actuators 1002-1007 may be a button or other actuator. Each of sensor actuators 1002-1007 may be electrically connected, wirelessly or via wires or other electrical connectors, to controller 667. Controller 667 may be configured to wirelessly communicate with control unit 106 and/or controller 390 of magnet assembly 140.

In some examples, each sensor actuator 1002-1007 may be an electromagnetic switch which turns on a respective electromagnet of magnet assembly 140. For example, each sensor actuator 1002-1007 may be associated with a separate magnet 401-416 and actuating a sensor actuator 1002-1007 may activate the corresponding magnet 401-416 and deactivating (e.g., releasing) a sensor actuator 1002-1007 may deactivate the corresponding magnet 401-416. In some examples, a plurality of sensor actuators 1002-1007 may be associated with one of magnets 401-416. In some examples, controller 667 may include a power source such as a battery. When one or more sensor actuators 1002-1007 are actuated, controller 667 may communicate with control unit 106 and/or controller 390 of magnet assembly 140 to activate one or more magnets 401-416, and when the one or more sensor actuators 1002-1007 is released the one or more magnets 401-416 may be deactivated by control unit 106 and/or controller 390.

FIG. 11 illustrates a magnified portion of second medical device 103 with cylindrical portion 556 engaging several sensor actuators 1002-1007 of sensor assembly 660. As shown in FIG. 11, since cylindrical portion 556 is positioned proximate to proximal end 1021 of sensor assembly 660, pivoting handle body 551 may cause cylindrical portion 556 to press on one or more sensor actuators 1002-1007. When one or more sensor actuators 1002-1007 are actuated, one or more magnets 401-416 may be activated and may create a magnetic field within and proximate to lumen 341 of magnet assembly 140. As shown in FIG. 12, when one or more magnets 401-416 are activated, the magnetic field created by the one or more magnets 401-416 may cause articulation section 535 to move towards or away from the activated magnets 401-416 because articulation section 535 may include a magnetic material, such as iron, steel, nickel, cobalt, etc. Articulation section 535 may be bent away from central longitudinal axis 150 of body 114 by the force applied to articulation section 535 from the magnetic field. Articulation section 535 will be discussed in further detail hereinbelow with regard to FIG. 16. In some examples, sufficient friction between ball portion 701 and receiving body 702 of ball joint 552 may prevent movement of cylindrical portion 556 relative to sensor actuators 1002-1007 and allow a user to release handle body 551 while maintaining engagement of cylindrical portion 556 with one or more sensor actuators 1002-1007.

Figures 13, 14, 15, 16, 17:
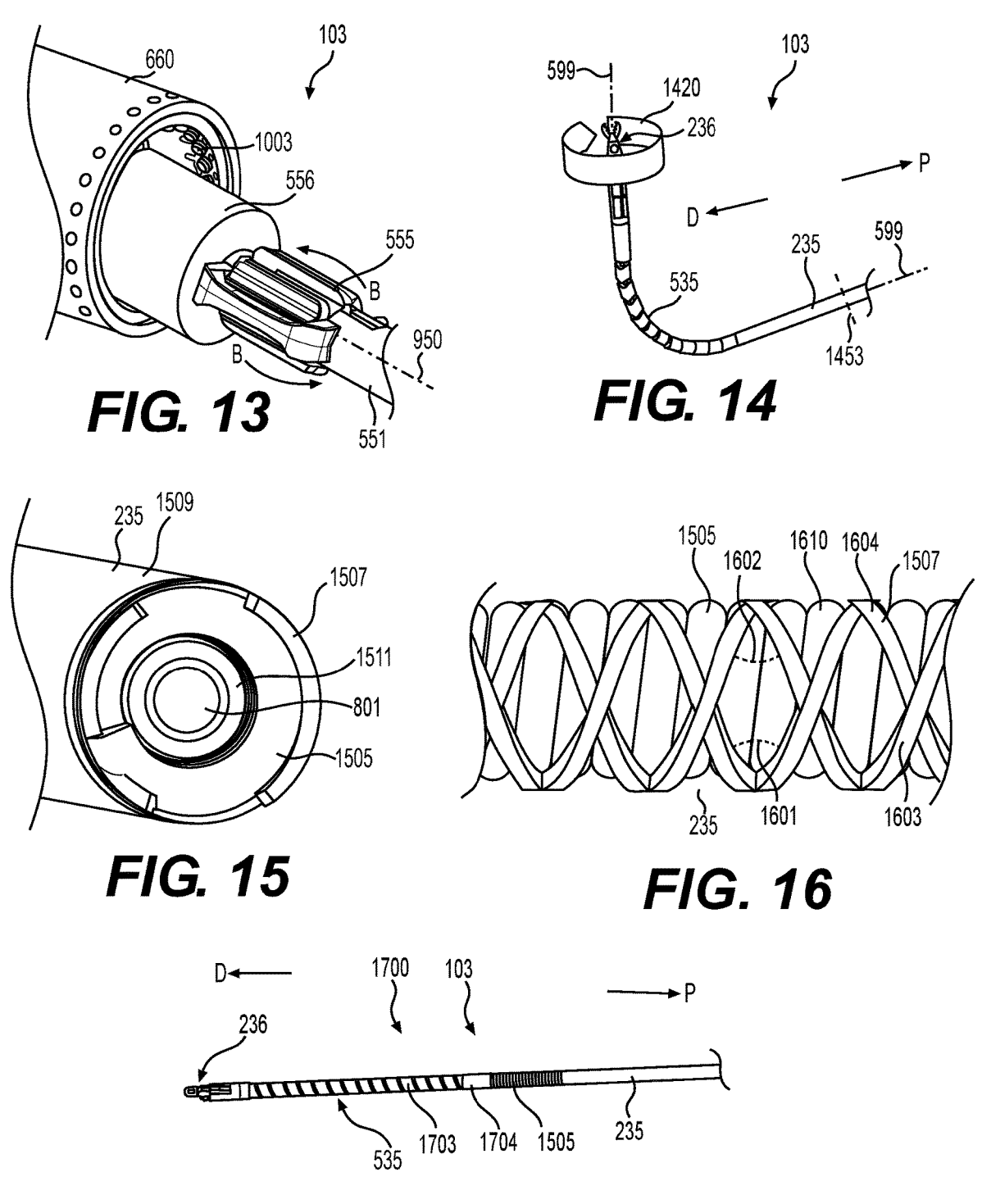
FIG. 13 is a perspective view of a portion of a medical device, according to aspects of the disclosure.
FIG. 14 is a perspective view of a distal portion of a medical device, according to aspects of the disclosure.
FIG. 15 illustrates a perspective view of the internal structure of a body of a medical device, according to aspects of the disclosure.
FIG. 16 illustrates a side view of an internal structure of a portion of a medical device, according to aspects of the disclosure.
FIG. 17 is a perspective view of a distal portion of a medical device, according to aspects of the disclosure.

FIG. 13 illustrates a magnified portion of second medical device 103 with cylindrical portion 556 engaging several sensor actuators 1002-1007 of sensor assembly 660, and arrows B showing rotation of second actuator 555 about central longitudinal axis 599 of handle body 551. FIG. 14 illustrates a corresponding distal portion of second medical device 103 for the position of handle body 551 shown in FIG. 13. As shown in FIG. 14, end effector 236, which is shown as a grasper, may rotate about axis 599 when second actuator 555 is rotated about axis 599. Arrow 1420 shows the rotation of end effector 236 relative to articulation section 535. Since cylindrical portion 556 is shown engaging one or more sensor actuators 1002-1007, articulation section 535 is shown bent which may be cause by the activation of one or magnets 401-416. End effector 236 may be rotatable relative to articulation section 535 and body 235.

FIG. 15 illustrates a portion of body 235 cut along axis 1453 to expose the interior layers within body 235. Body 235 may be a plastic member 1509 forming a tubular body with a central lumen extending longitudinally through body 235. Actuation wire 801 may be positioned within a central portion of body 235. A liner layer 1511 may be a tubular body configured to receive actuation wire 801 and be configured to allow actuation wire 801 to move proximally and distally through liner layer 1511. In some examples, liner layer 1511 may comprise Polytetrafluoroethylene (PTFE).

A coil 1505 may extend circumferentially around liner layer 1511 and may extend longitudinally from ball joint 552 to the proximal end of articulation section 535. Coil 1505 may be configured to provide compressive stiffness for force transfer from the proximal end to distal end of second medical device 103, and provide torsional stiffness to increase torque transfer from the proximal end to distal end of medical device 103. In some examples, coil 1505 may be made of a wire with a diameter from 0.013"-0.041". In some examples, coil 1505 may be a stainless steel coil. The pitch of coil 1505 may be the same as the diameter of the wire that forms coil 1505. In some examples, the wire of coil 1505 may have a diameter of 0.021" and the pitch of coil 1505 may be 0.021". The angle formed between the wire of coil 1505 and a central longitudinal axis of coil 1505 may range from 90 degrees to 120 degrees.

A braid layer 1507 may extend around coil 1505 and may be formed with a plurality of wires 1603, 1604 (shown in FIG. 16). Braid layer 1507 may extend from ball joint 552 to the proximal end of articulation section 535, and may abut the radially-outward facing surface 1610, relative to central axis 599, of coil 1505. FIG. 16 illustrates a side view of braided layer 1507 positioned over coil 1505, with body 235 removed. The wires 1603, 1604 may be flat or round. Braided layer 1507 may be formed over coil 1505 from wires 1603, 1604 with different braiding patterns, such as a diamond braid, regular braid, or a Hercules braid. Although braid layer 1507 is shown with two wires 1603, 1604 in FIG. 16, braid layer 1507 is not so limited and may be formed using any suitable number of wires 1603, 1604. A pic count of 40-80 may be used in braid layer 1507. In some examples, braid angles 1601, 1602 may vary between 35 degrees and 50 degrees. In some examples, the difference between braid angle 1601 and braid angle 1602 may not be greater than 5 degrees.

FIG. 17 illustrates a distal portion 1700 of second medical device 103 including body 235, a coupler 1704, articulation section 535, and end effector 236. A portion of body 235 is removed in FIG. 17 to expose coil 1505. The distal end of coil 1505 and body 235 may be coupled to coupler 1704, and a proximal end of articulation section 535 may be coupled to coupler 1704. Coupler 1704 may be cylindrical and may be fixedly coupled to liner layer 1511, coil 1505, and body 235. Actuation wire 801 may extend through coupler 1704 and articulation section 535 to end effector 236. Articulation section 535 may be made of a magnetic material, such as a ferromagnetic material like iron, steel, nickel, cobalt, neodymium, etc. Articulation section 535 may be formed with a rectangular strip 1703 of magnetic material wound into a helix, which may facilitate bending articulation section 535. In some examples, articulation section 535 may be biased towards a neutral position in which articulation section 535 is straight and aligned with central longitudinal axis 599. End effector 236 may be a non-magnetic material, such as stainless steel or aluminum.

In operation, a user may first position a patient 160 on patient table 105. The user may then position first medical device 102 and second medical device 103 within two separate working channels of endoscope 101, and then position distal portion 116 of endoscope 101 at a target area within the body of patient 160. In some examples, a magnetic shield 231 may be placed over the distal end of endoscope 101 before insertion of endoscope 101 into the patient's body. Once distal portion 116 is positioned at the target area, the user may move magnet assembly 140 to a position in which magnet assembly 140 is aligned with the target area. For example, the user may push/pull magnet assembly 140 along rail portions 310, 311 of patient table 105 to position magnet assembly 140 proximate to the target area. The user may then grasp tissue by pushing second medical device 103 distally to abut tissue, and moving first actuator 554 proximally relative to handle body 551 to close the grasper. The user may then pivot handle body 551 about ball joint 552 and actuate one or more sensor actuators 1002-1007 with cylindrical portion 556. The actuation of sensor actuators 1002-1007 may then activate one or more magnets 401-416 of magnet assembly 140, and articulation section 535 may move and/or bend from the force applied by the magnetic field created by the one or more activated magnets 401-416.

The user may then rotate the grasper by rotating second actuator 555. Once tissue is appropriately positioned by the user with second medical device 103, the user may then articulate first medical device 102 to cut the tissue. In some examples, the user may apply electrical energy to end effector 234 of first medical device 102 to cut the tissue. The user may then deactivate the one or more magnets 401-416 by pivoting handle body 551 away from the sensor actuators 1002-1007 to deactivate the one or more sensor actuators 1002-1007, which may then deactivate the one or more magnets 401-416. In some examples, articulation section 535 may move to a neutral position when the one or more magnets 401-416 are deactivated.

Although the use of second medical device 103 as part of medical system 100 is discussed hereinabove, second medical device 103 is not so limited. For example, second medical device 103 may be used without first medical device 102. In some examples, second medical device 103 may not include a grasper as end effector 236 and may include any other end effector known in the art, such as a cutting knife, a snare, a basket, or an electrocautery element.

It also should be understood that one or more aspects of any of the medical devices, systems, and methods described herein may be used for grasping, cutting, dissecting, treating, ablating, or otherwise manipulating tissue in any part of the human body. For example, any of the medical devices described herein may be used in medical procedures such as for Endoscopic Submucosal Dissection (ESD), cancer treatment, kidney or bladder biopsies or resections, and/or other procedures where removal, resection, dissection, fulguration, and/or ablation of tissue is needed.

Various aspects discussed herein may help reduce procedure time, increase tissue treatment effectiveness, reduce the risks to the subject, etc. Various systems and devices discussed herein may eliminate the need for articulation wires extending through an endoscopic tool while still enabling a user to articulate a distal portion of the device while the distal portion is positioned within a body of a patient.

Various aspects discussed herein may enable a endoscopic tool to have six degrees of freedom or more while only including a single actuation wire extending through the tool and without any articulation wires extending through the tool.

Although the exemplary embodiments described above have been disclosed in connection with medical devices for manipulating and cutting human tissue through one or more working channels of a medical device, a natural orifice, or by incision, a person skilled in the art will understand that the principles set out above can be applied to any medical device or medical method and can be implemented in different ways without departing from the scope of the disclosure as defined by the claims. In particular, constructional details, including manufacturing techniques and materials, are well within the understanding of those of skill in the art and have not been set out in any detail here. These and other modifications and variations are well within the scope of this disclosure and can be envisioned and implemented by those of skill in the art.

Moreover, while specific exemplary embodiments may have been illustrated and described collectively herein, it should be appreciated that any subsequent arrangement designed to achieve the same or similar purpose may be substituted for the specific embodiments described and shown herein. This disclosure is intended to cover any and all subsequent adaptations or variations of various embodiments. Combinations of the above embodiments, and other embodiments not specifically described herein, will be apparent to those of skill in the art upon reviewing the description.

It should be appreciated that the disclosed devices, for example control unit 106 or controllers 390, 667, may include various suitable computer systems and/or computing units incorporating a plurality of hardware components, such as, for example, a processor and non-transitory computer-readable medium that allow the devices to perform one or more operations during a procedure in accordance with those described herein. Other aspects of the disclosure will be apparent to those skilled in the art from consideration of the specification and practice of the features disclosed herein. It is intended that the specification and examples be considered as exemplary only.

It should be appreciated that the various systems may include any computing device. The computing device may include input and output ports to connect with input and output devices such as keyboards, mice, touchscreens, monitors, displays, etc. Of course, the various system functions may be implemented in a distributed fashion on a number of similar platforms, to distribute the processing load. Alternatively, the systems may be implemented by appropriate programming of one computer hardware platform.

In one embodiment, any of the disclosed systems, methods, and/or graphical user interfaces may be executed by or implemented by a computing system consistent with or similar to the descriptions herein. Although not required, aspects of this disclosure are described in the context of computer-executable instructions, such as routines executed by a data processing device, e.g., a server computer, wireless device, and/or personal computer. Those skilled in the relevant art will appreciate that aspects of this disclosure can be practiced with other communications, data processing, or computer system configurations, including: Internet appliances, hand-held devices (including personal digital assistants ("PDAs")), wearable computers, all manner of cellular or mobile phones (including Voice over IP ("VoIP") phones), dumb terminals, media players, gaming devices, virtual reality devices, multi-processor systems, microprocessor-based or programmable consumer electronics, set-top boxes, network PCs, mini-computers, mainframe computers, and the like. Indeed, the terms "computer," "computing device," and the like, are generally used interchangeably herein, and refer to any of the above devices and systems, as well as any data processor.

Aspects of this disclosure may be embodied in a special purpose computer and/or data processor that is specifically programmed, configured, and/or constructed to perform one or more of the computer-executable instructions explained in detail herein. While aspects of this disclosure, such as certain functions, are described as being performed exclusively on a single device, this disclosure may also be practiced in distributed environments where functions or modules are shared among disparate processing devices, which are linked through a communications network, such as a Local Area Network ("LAN"), Wide Area Network ("WAN"), and/or the Internet. Similarly, techniques presented herein as involving multiple devices may be implemented in a single device. In a distributed computing environment, program modules may be located in both local and/or remote memory storage devices.

Aspects of this disclosure may be stored and/or distributed on non-transitory computer-readable media, including magnetically or optically readable computer discs, hard-wired or preprogrammed chips (e.g., EEPROM semiconductor chips), nanotechnology memory, biological memory, or other data storage media. Alternatively, computer implemented instructions, data structures, screen displays, and other data under aspects of this disclosure may be distributed over the Internet and/or over other networks (including wireless networks), on a propagated signal on a propagation medium (e.g., an electromagnetic wave(s), a sound wave, etc.) over a period of time, and/or they may be provided on any analog or digital network (packet switched, circuit switched, or other scheme).

Program aspects of the technology may be thought of as "products" or "articles of manufacture" typically in the form of executable code and/or associated data that is carried on or embodied in a type of machine-readable medium. "Storage" type media include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer of the mobile communication network into the computer platform of a server and/or from a server to the mobile device. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links, or the like, also may be considered as media bearing the software. As used herein, unless restricted to non-transitory, tangible "storage" media, terms such as computer or machine "readable medium" refer to any medium that participates in providing instructions to a processor for execution.

While principles of the disclosure are described herein with reference to illustrative aspects for particular applications, it should be understood that the disclosure is not limited thereto. Those having ordinary skill in the art and access to the teachings provided herein will recognize additional modifications, applications, aspects, and substitution of equivalents all fall within the scope of the aspects described herein. Accordingly, the disclosure is not to be considered as limited by the foregoing description.

Other exemplary embodiments of this disclosure will be apparent to those skilled in the art from consideration of the specification and practice of the exemplary embodiments disclosed herein. It is intended that the specification and examples be considered as exemplary only, and departures in form and detail may be made without departing from the scope and spirit of this disclosure as defined by the following claims.

I claim:

1. A medical device for insertion into a body, the medical device comprising:
a handle assembly including a handle body and a ball joint;
a sensor assembly configured to electronically communicate with a magnet, wherein the ball joint is positioned within the sensor assembly;
a body extending longitudinally from the handle assembly;
an articulation portion coupled to a distal end of the body, wherein the articulation portion includes a magnetic material; and
an end effector coupled to a distal end of the articulation portion;
wherein the articulation portion is configured to move upon application of a magnetic field from the magnet.

2. The medical device of claim 1, wherein the sensor assembly comprises:
a cylindrical body including a central lumen, wherein a portion of the handle assembly is positioned within the central lumen; and
a plurality of sensor actuators positioned facing the handle assembly.

3. The medical device of claim 2, wherein the handle assembly includes a cylindrical portion configured to actuate one or more of the plurality of sensor actuators when the handle body is pivoted towards the sensor assembly.

4. The medical device of claim 2, wherein the plurality of sensor actuators are evenly spaced circumferentially around a central longitudinal axis of the handle assembly.

5. The medical device of claim 1, wherein the handle assembly includes a first actuator and a second actuator, and wherein each of the first actuator and the second actuator engage a single actuation wire.

6. The medical device of claim 1, wherein the sensor assembly includes a controller configured to wirelessly communicate with a controller associated with the magnet.

7. The medical device of claim 1, wherein the body comprises:
a coil,
a braid layer extending around the coil,
an exterior layer extending around the braid layer, and
a central lumen configured to receive an actuation wire.

8. The medical device of claim 1, wherein the articulation portion includes a rectangular strip of magnetic material wound in a helical shape.

9. The medical device of claim 1, wherein the end effector includes stainless steel or Nitinol.

10. The medical device of claim 1, wherein the handle body includes:
a ball portion at a distal end of the handle body;
a cylindrical portion coupled to the ball portion;
a first slot configured to receive a first actuator;
a second slot configured to receive a second actuator; and
a ring portion at a proximal end of the handle body.

11. The medical device of claim 10, wherein the sensor assembly comprises:
a cylindrical body including a central lumen, wherein a portion of the handle assembly is positioned within the central lumen; and
a plurality of sensor actuators positioned on the cylindrical body and facing the handle assembly, wherein the plurality of sensor actuators are positioned around the cylindrical portion and proximal from the ball joint.

12. The medical device of claim 1, further comprising an articulation wire extending from the end effector, through the body and the sensor assembly, and coupled to a portion of the handle assembly.

13. The medical device of claim 1, wherein the handle assembly is configured to pivot relative to the sensor assembly.

14. The medical device of claim 1, wherein the end effector is rotatable, about a central longitudinal axis of the medical device, relative to the articulation portion.

15. A medical system comprising:
a medical device comprising:
a handle assembly;
a sensor assembly configured to communicate with a magnet assembly and coupled to the handle assembly;
a body extending longitudinally from the handle assembly; and
an articulation portion coupled to a distal end of the body, wherein the articulation portion is made of a magnetic material; and
the magnet assembly moveably coupled to a patient table and comprising a plurality of magnets, wherein the plurality of magnets are positioned circumferentially around the patient table;
wherein the articulation portion is configured to move when the magnet assembly applies a magnetic field to the articulation portion.

16. The medical system of claim 15, wherein the sensor assembly includes a plurality of sensor actuators, and wherein each sensor actuator is in electronic communication with at least one magnet of the plurality of magnets.

17. A method of moving a medical device, the method comprising:
pivoting a handle assembly about a ball joint;
engaging at least one sensor actuator of a sensor assembly with the handle assembly;
activating an electromagnet via the engaged at least one sensor actuator; and
moving an articulation section via a magnetic field induced by activating the electromagnet, wherein the articulation section is a magnetic material.

18. The medical device of claim 17, further comprising:
positioning a magnet assembly proximate to a target area, wherein the articulation section is positioned at the target area and the magnet assembly includes the electromagnet.

* * * * *